(12) United States Patent
Volland et al.

(10) Patent No.: US 8,637,278 B2
(45) Date of Patent: Jan. 28, 2014

(54) METHOD FOR THE ENZYMATIC PRODUCTION OF EMULSIFIERS CONTAINING MONO- AND DIACYLGLYCERIDES

(75) Inventors: Michael Volland, Karlsfeld (DE); Thomas Lötzbeyer, Eching (DE); Volker Sieber, Nandlstadt (DE); Eva Wittmann, Traunreut (DE)

(73) Assignee: Satia GmbH, Freising (DE)

( * ) Notice: Subject to any disclaimer, the term of this patent is extended or adjusted under 35 U.S.C. 154(b) by 2053 days.

(21) Appl. No.: 10/570,613

(22) PCT Filed: Sep. 2, 2004

(86) PCT No.: PCT/EP2004/009800
§ 371 (c)(1),
(2), (4) Date: Mar. 3, 2006

(87) PCT Pub. No.: WO2005/024036
PCT Pub. Date: Mar. 17, 2005

(65) Prior Publication Data
US 2007/0009644 A1    Jan. 11, 2007

(30) Foreign Application Priority Data
Sep. 4, 2003 (DE) ................. 103 40 739

(51) Int. Cl.
*C12P 7/62* (2006.01)
(52) U.S. Cl.
USPC .............................. 435/135; 435/41; 435/198
(58) Field of Classification Search
USPC .......................................... 435/41, 135, 198
See application file for complete search history.

(56) References Cited

U.S. PATENT DOCUMENTS

| | | | | |
|---|---|---|---|---|
| 5,378,623 A | * | 1/1995 | Hattori et al. | 435/198 |
| 5,591,615 A | * | 1/1997 | Oester et al. | 435/448 |
| 5,888,562 A | * | 3/1999 | Hansen et al. | 426/45 |
| 6,162,623 A | * | 12/2000 | Grote et al. | 435/134 |
| 6,410,480 B1 | * | 6/2002 | Muhlebach et al. | 504/105 |
| 2004/0006096 A1 | * | 1/2004 | Muller et al. | 514/269 |
| 2004/0091574 A1 | * | 5/2004 | Soe | 426/33 |
| 2004/0166215 A1 | * | 8/2004 | Heroufosse et al. | 426/321 |

FOREIGN PATENT DOCUMENTS

| | | |
|---|---|---|
| DE | 1900959 | 1/1969 |
| DE | 19623735 | 10/1997 |
| JP | 63042691 A * | 2/1988 |
| JP | 63302929 A * | 12/1988 |
| WO | WO 9106661 | 5/1991 |
| WO | WO 0052190 | 9/2000 |

OTHER PUBLICATIONS

English abstract of JP 63042691 (Feb. 23, 1988) downloaded from Derwent Feb. 11, 2011.*
English translation of JP 63302929 (Dec. 9, 1988).*
Tweddell et al. Biotechnol. Lett. (1997) 19(9): 939-942.*
English translation for JP 03109935 Aug. 2011 by FLS Inc.*
Suzuki Kazuaki et al.; Production Fo Emulsifier Composition; Abstract in English for JP3109935A downloaded from www.Thomsoninnovation.com on Jun. 16, 2011.

* cited by examiner

*Primary Examiner* — Susan Hanley

(57) ABSTRACT

The invention relates to a method for the enzymatic production of emulsifiers containing mono- and diacylglycerides. In a first step a), a mixture of a phospholipid component and a triacylglyceride component is prepared, then in step b) a quantity of an aqueous solution containing a (phospho)lipase is added to the mixture obtained, to produce a water content of the mixture of between 3 and 15 wt. %. In a subsequent step c), the mixture obtained in the previous step is reacted at a temperature ranging between 20° and 80° C. over a period of at least two hours and said mixture is then dried.

17 Claims, No Drawings

METHOD FOR THE ENZYMATIC PRODUCTION OF EMULSIFIERS CONTAINING MONO- AND DIACYLGLYCERIDES

The present invention relates to a method for the enzymatic production of emulsifiers containing mono- and diacylglycerides and use thereof.

Lecithins and lysolecithins are used in various applications as emulsifiers. They are found in foods, cosmetics, food supplements and chemical formulations. They are generally obtained as byproducts of oil isolation, e.g. from soybeans or rapeseed, or are extracted directly from the corresponding raw material, for example egg yolk. Lecithins and lysolecithins are usually a complex mixture of phospholipids (1,2-diacylglycerol phosphate), lysophospholipids (1- or 2-monoacylglycerol phosphate as hydrolysis derivative of phospholipids), glycolipids and triacylglycerides. Depending on the production process, the contents of the individual fractions can vary greatly in the end product.

Crude lecithin is a non-standardized lecithin, as occurs, e.g., as byproduct in the oil mill during the refining of vegetable oil. The expression oil comprises refined or unrefined vegetable oil, partially or completely hardened (hydrogenated) vegetable oil or animal fat, all of the main components of which are triacylglycerides.

Mono-, di- and triacylglycerides have one, two or three acyl groups which are derived from a long-chain saturated or monounsaturated or polyunsaturated fatty acid. Preferably, the acyl groups have 6 to 35 carbon atoms, in particular 10 to 30 carbon atoms, and still more preferably 12 to 26 carbon atoms. Monoacylglycerides can be 1- or 2-monoacylglycerides, di-glycerides can be 1,2- or 1,3-diacylglycerides.

Higher contents of lysolecithins can be obtained using an enzymatic hydrolysis of the corresponding phospholipids by eliminating one or two fatty acid residues to give the corresponding lysophospholipids.

"Lysolecithin" in the present context, as also in the commercial and food law meaning, is to be taken to mean a mixture of partially enzymatically hydrolyzed polar lipids and neutral lipids which have an acetone-insoluble fraction of at least 56%. Acetone-insoluble is one of the most important analytical parameters which is used for the assessment of lecithin in the food law meaning and describes the fraction of polar lipids in lecithin which are insoluble in acetone.

The hydrolysis of lipids and phospholipids using lipases and phospholipases is described well (Adlercreutz, Patrick, 1994: "Enzyme-catalyzed lipid modification"; Biotechnology & Genetic Engineering Reviews 12, 231-254).

In addition, a multiplicity of patent documents are likewise concerned with the enzymatic hydrolysis of phospholipids to lysolecithins.

EP-A 260573 describes the production of lysolecithin by admixing a lecithin with 5-30% by weight of water and reacting it in the presence of a calcium salt and also of a lecithin-hydrolyzing enzyme to form lysolecithin.

WO 91/03565 teaches the hydrolysis of isolated phospholipids in organic solvents using an immobilized lipase, whereas EP-A 870840 describes the hydrolysis of an aqueous lecithin solution using phospholipases in which the resultant lysophospholipids are freed from accompanying matter by solvent extraction (acetone).

A further method for the production of a lysolecithin is described in JP 10042884, where the desired product is produced by hydrolysis of lecithin by means of phospholipase A2 in a solvent/water mixture.

WO 97/28270 teaches a method for producing lysophosphatidylcholine from the substrate phosphatidylcholine using a phospholipase A2. The reaction is carried out in a dispersion of the substrate with a further agent from the group of the monoacylglycerides, diacylglycerides, polyglycerol, sucrose and sorbitan esters of fatty acids, and also glycerol, in the presence of water.

In addition to the lecithins and lysolecithins, mono- and diacylglycerides also act as stabilizers for emulsions. They are usually obtained by alkaline saponification of triacylglycerides at high temperatures. However, they must be cost-intensively purified after this hydrolysis step.

An alternative method for producing monoacylglycerides is described by WO 02/11543. Using a lipase, from the corresponding triacylglyceride, over 40% is obtained as monoacylglycerides in a polyol/water mixture. Lecithin, and also fats, are added here solely to expand the substrate spectrum.

Generally, the mono- and diacylglycerides are used for stabilizing emulsions in combination with lysolecithins in the bakery product and margarine sector. For this, hitherto the individual components are usually produced separately, purified and mixed in the desired concentration.

WO 00/52190 describes a method for producing a mixture of lysolipids, lysophospholipids, monoacylglycerides and diacylglycerides by reacting lecithin in a water/polyol mixture in the presence of a combination of lipase and phospholipase. The focus in this case is on as complete as possible reaction of the phospholipids at a conversion rate of 80% based on the ratio of lysophosphatidylcholine/phosphatidylcholine. Owing to the high water content of the reaction solution of approximately 60%, the production of the end product, however, is associated with high energy consumption and costs. A defined setting of the lysolecithin/mono- and diacylglyceride ratio is at any rate not possible using this method, since the lysophospholipid fraction always predominates and the monoacylglyceride fraction, owing to the addition of the glycerol, always ends significantly higher than the diacylglyceride fraction.

However, the ratio between mono- and diacylglycerides and also lysophospholipids in the product to be stabilized can vary greatly depending on the respective application. For instance, to stabilize margarine, for example, mono-/diacylglycerides and lysolecithin are added in the ratio 1.7:1, whereas in the bakery product sector, the fraction of lysolecithin predominates and the resultant mixture is present in the ratio of 0.4:1.

Starting from this state of knowledge, the object set for the present invention is to provide a method for the enzymatic production of emulsifiers containing mono- and diacylglycerides which permits an inexpensive production of mixtures of mono- and diacylglycerides and also lysophospholipids without the otherwise customary addition of calcium, polyols or organic solvents and which, in addition, allows flexible setting of the ratio between mono- and diacylglycerides and also lysophospholipids by varying the composition of the reaction mixture or the reaction conditions.

This object is achieved by a corresponding method in which
  a) a mixture of a phospholipid component and a triacylglyceride component is charged,
  b) an amount of an aqueous solution containing (phospho) lipase is added to the mixture from method step a) such that the water content of the mixture is between 3 and 15% by weight, and in particular between 5 and 12% by weight, subsequently c) the mixture obtained from method step b) is reacted at temperatures between 20° C. and 80° C. for a period of at least 2 hours, and finally d) the mixture is dried after the end of the reaction.

Surprisingly, in the inventive simultaneous reaction of phospholipids (lecithin) and triacylglycerides (oil) to form lysophospholipids and mono- and also diacylglycerides, it is proved that, by selecting the parameters temperature, incubation time, ratio between lecithin and oil, lecithin and water and also oil and water and/or the amount of enzyme added, the composition of the reaction product can be set exactly. For instance, it is possible, e.g. via the ratio of lecithin to oil which may be defined via the acetone-insoluble fraction, in the case of a hydrolysis using lipase and a defined water fraction, to set the fraction of monoacylglycerides and 1,2-diacylglycerides of the total mono-/diacylglyceride fraction in a targeted manner with comparatively constant fraction of 1,3-diacylglycerides. However, alternatively, via the incubation time, for example at a temperature of 60° C., in the presence of 0.05% by weight of lipase in a mixture of crude lecithin/oil, having an acetone-insoluble fraction of 50%, and having a water fraction of 10%, the fraction of monoacylglycerides and 1,3-diacylglycerides of the total mono-/diacylglyceride fraction can be varied, the fraction of 1,2-diacylglycerides of the total mono-/diacylglyceride content remaining comparatively constant. These advantages were unexpected to this extent, taking into account the simplicity of the method procedure.

As phospholipid component, according to the invention a lecithin, and preferably crude lecithin, has been found to be particularly suitable, a crude soy lecithin being considered as particularly preferred.

Vegetable and/or animal oils, preferably in refined and/or at least partially hardened form, are, in the context of the present invention, particularly suitable representatives of the triacylglyceride component, as is charged in method step a).

With respect to the method procedure, in a special variant, in method step a) a mixture can be charged which has a phospholipid component fraction between 10 and 80% by weight and/or a triacylglyceride component fraction between 20 and 90% by weight. The weight ratio between phospholipid component fraction and triacylglyceride component fraction is advantageously 1:0.25 to 1:4.

In general, method step a) is not subject to any particular restriction, but, under certain conditions, it can be advantageous that the mixture in method step a) is brought to a temperature between 35° C. and 60° C., which the present invention likewise takes into account.

With respect to method step b), it is to be considered as preferred if use is made of a lipase and/or phospholipase of microbial origin, preferably from *candida* and/or *aspergillus*. Particularly suitable strains here are *Aspergillus niger* and *Candida cylindracea*, in which case, obviously, any other suitable enzyme source can also be selected.

As already stated, a great advantage of the present method is that the ratio of mono- and diacylglycerides can be set in a targeted manner in the product having an emulsifying action. The invention therefore also provides that in method step b) use is made of a phospho(lipase) amount of 0.05 to 10.0 mg per ml of reaction mixture, and in particular 0.1 to 5 mg per ml of reaction mixture. The desired amount of enzyme in each case can of course also be used as a function of the enzyme activity, for which reason a corresponding amount between 0.1 and 120 u per ml of reaction mixture is advisable. Generally, the ratio of lipase to phospholipase in the enzyme component used can be varied in a broad range, by which means the composition of the product obtained (the emulsifier) can be affected in a targeted manner.

With respect to method step c), a temperature is to be considered as preferred which is between 40° C. and 50° C. The reaction period in method step c) should advantageously be between 5 and 20 hours, and particularly preferably between 8 and 12 hours.

The final drying step d) in the present method is again not at all limiting and can be carried out using any customary method. At any rate, care should be taken to ensure gentle conditions, for which reasons temperatures are particularly suitable which are between 60° C. and 80° C. Carrying out the drying in a vacuum is particularly advisable.

Typically, the inventive method is carried out by combining lecithin with oil in a specific ratio, heating to a temperature between 35° C. and 60° C., and mixing it by stirring. A possible source of the lecithin here is crude lecithin from soy, it being also possible to use, instead of crude lecithin, a standardized, deoiled or fractionated lecithin. As oil, vegetable oils, e.g. soy oil, or a hydrogenated vegetable oil, e.g. palm fat, or else animal oils and fats, come into consideration. The enzyme component is added to the lecithin/oil mixture as lipase in an aqueous solution, the total amount of water preferably being in the range of 6 to 12% by weight. Possible sources of lipase enzymes are, in particular, *Candida cylindracea* (see Biocatalysts, Pontypridd, Wales) or *Aspergillus niger* (see Amano, Nagoya, Japan). The reaction mixture is then stirred at a defined temperature and for a defined time, the temperature being able to be, e.g., in the range of 50° C. As an incubation time, preferably a period between 2 and 15 hours is provided. After the completion of this reaction, the mixture is dried under a vacuum at a temperature of approximately 70° C., and the product, if appropriate, is further crystallized.

As a preferred product, a mixture is claimed by the present invention which comprises lysolecithin, mono- and diacylglycerides, the preferred fractions being with respect to lysolecithin between 3.0 and 55% by weight and with respect to the monoacylglycerides between 2.0 and 20% by weight. With respect to the diacylglyceride fraction, amounts are recommended which are between 6.0 and 40% by weight.

Alternatively, the invention, as product from the claimed method, provides a mixture in which the ratio of phospholipid component to the combined mono- and diacylglyceride component is 1:0.25 to 4.0.

The reaction products, after drying, can be used directly as emulsifiers in standard methods for producing margarine or baking mixtures. In this case, no addition of further components, e.g. additional mono- or diacylglycerides, is necessary.

In addition to the method itself and the mixtures produced therewith, the present invention also claims the use of the mixtures which can be produced by the method for producing emulsions and creams in the food sector, in particular in the form of ice creams, margarines and bakery products, and in the cosmetics sector.

In the context of this invention, finally it has been found that the products and thus the emulsifier, in contrast to the emulsifiers previously available which are produced by mixing the pure lysolecithin and mono- and diacylglyceride components, can also be in liquid form, and which are therefore readily usable without further treatment, without suffering quality impairments.

By means of the claimed method, emulsifiers are successfully produced simply by the simultaneous enzymatic reaction of phospholipids (lecithin) and triacylglycerides (oil) to give lysophospholipids and mono-/diacylglycerides. The conversion of lecithin to lysolecithin is performed here via an enzymatic hydrolysis without organic solvents, polyols and/or calcium having to be added for this, or a water fraction >15% by weight needing to be used. In addition, in the context of the inventive method, exact setting of the fractions of individual lipid components in the product is possible accurately by varying selected input parameters. Finally, a further advantage of the invention is considered to be that the resultant emulsifiers can also be isolated directly in liquid form.

In the case of the described method for the enzymatic production of emulsifiers containing mono- and diacylglycerides, in a first method step a) a mixture of a phospholipid component and a triacylglyceride component is charged, then, in method step b) an amount of an aqueous solution containing (phospho)lipase is added to the mixture from method step a) such that the water content of the mixture is between 3 and 15% by weight. Subsequently, in method step c) the mixture obtained from the previous step is reacted at temperatures between 20° C. and 80° C. for a period of at least 2 hours, and finally this mixture is dried. Particularly suitable components have proved to be crude soy lecithin and vegetable and/or animal oils which are reacted together with a mixture of lipase and/or phospholipase as enzyme component. By means of this method which succeeds without the otherwise customary organic solvents, polyols or ionic additives and also using a low water fraction, emulsifiers are obtained, the lysophospholipid and mono-/diacylglyceride composition of which can be set in a targeted manner. These emulsifiers, which are also obtainable in liquid form, are used in the food and cosmetics sectors.

The examples hereinafter illustrate said advantages of the claimed method for the enzymatic production of emulsifiers.

EXAMPLES

The crude lecithin used in the examples hereinafter originated from Honeymead, USA; as soy oil, use was made of freely available commercially conventional products.

The composition of the product obtained in each case was analyzed using HPLC, HPTLC and gravimetric methods. For HPLC, as stationary phase, use was made of a silica gel Si60 column. The mobile phase was composed of n-hexane/2-propanol/water (0.25/4/1 [v/v/v]) which was added to the column at a flow rate of 1.2 ml/min. The contents of phosphatidylcholine and lysophosphatidylcholine could be quantified on the basis of the different retention times. The samples had been previously dissolved in n-hexane/2-propanol (2/1 [v/v]). HPTLC was carried out using silica gel Si60 applied to a glass plate (shape 20×10 cm) as stationary phase. As mobile phase, use was made of diethyl ether/petroleum spirit/glacial acetic acid in the ratio 40/59/1 [v/v/v]. After the analytical run and drying of the plates, the resultant bands were derivatized using a copper(II) sulfate solution (10% by weight copper sulfate dissolved in 8% strength phosphoric acid) and the content of monoacylglycerides and also 1,2- and 1,3-diacylglycerides was quantified. The samples had been previously dissolved in chloroform.

The gravimetric method was used to determine the acetone-insoluble fraction. In this case the sample was admixed with acetone, the resultant residue was separated off, dried and weighed.

Example 1

45 g of crude lecithin were mixed with 55 g of soy oil and stirred at a temperature of 47.5° C. 0.13 g of lipase from *Candida cylindracea* (from Biocatalysts, UK) were dissolved in 9 g of water and subsequently added, with stirring, to the lecithin/oil mixture. This mixture was stirred at 47.5° C. and, after a reaction time of 8.5 h, dried under a vacuum of 0.1 bar and at a temperature of 80° C.

Result:

The resultant product had an acetone-insoluble fraction of 28% by weight which corresponds to a lecithin fraction of 43%, and in addition 2% by weight of lysophosphatidylcholine, 4.5% by weight of monoacylglycerides and 11% by weight of diacylglycerides. The ratio of lecithin to mono-/diacylglycerides was 1:0.34.

Example 2

135 g of crude lecithin were mixed with 165 g of soy oil and 27 g of water and stirred at a temperature of 47.5° C. 0.15 g of lipase from *Candida cylindracea* were added, with stirring, to the lecithin/oil mixture. This mixture was stirred at 47.5° C. and, after a reaction time of 8.5 h, dried under a vacuum of 0.1 bar and at a temperature of 80° C.

Result:

The resultant product had an acetone-insoluble fraction of 27% by weight which corresponds to a lecithin fraction of 42%, and in addition, 2.5% by weight of lysophosphatidylcholine, 5% by weight of monoacylglycerides and 10% by weight of diacylglycerides. The ratio of lecithin to mono-/diacylglycerides was 1:0.36.

Example 3

10 g of crude lecithin were mixed with 90 g of soy oil and stirred at a temperature of 35° C. 0.1 g of lipase from *Candida cylindracea* was dissolved in 12 g of water and subsequently added, with stirring, to the lecithin/oil mixture. This mixture was stirred at 35° C. and, after a reaction time of 15 h, dried under a vacuum of 0.1 bar and at a temperature of 60° C.

Result:

The resultant product had an acetone-insoluble fraction of 6% by weight, which corresponds to a lecithin fraction of 9.5%, and in addition 0.2% by weight of lysophosphatidylcholine, 4% by weight of monoacylglycerides and 10% by weight of diacylglycerides. The ratio of lecithin to mono-/diacylglycerides was 1:1.5.

Example 4

30 g of crude lecithin were mixed with 270 g of soy oil and stirred at a temperature of 60° C. 0.3 g of lipase from *Candida cylindracea* was dissolved in 18 g of water and subsequently added, with stirring, to the lecithin/oil mixture. This mixture was stirred at 60° C. and, after a reaction time of 15 h, dried under a vacuum of 0.1 bar and at a temperature of 80° C.

Result:

The resultant product had an acetone-insoluble fraction of 6% by weight which corresponds to a lecithin fraction of 9.5%, and in addition 0.2% by weight of lysophosphatidylcholine, 2% by weight of monoacylglycerides and 12% by weight of diacylglycerides. The ratio of lecithin to mono-/diacylglycerides was 1:1.5

Example 5

70 g of crude lecithin were mixed with 30 g of soy oil and stirred at a temperature of 35° C. 0.1 g of lipase from *Candida cylindracea* was dissolved in 12 g of water and subsequently added, with stirring, to the lecithin/oil mixture. This mixture was stirred at 35° C., and, after a reaction time of 2 h, dried under a vacuum of 0.1 bar and at a temperature of 60° C.

Result:

The resultant product had an acetone-insoluble fraction of approximately 45% by weight and it contained 3% by weight of lysophosphatidylcholine, 6.5% by weight of monoacylglycerides and 9% by weight of diacylglycerides.

Example 6

75 g of crude lecithin were mixed with 25 g of soy oil and stirred at a temperature of 47.5° C. 0.05 g of lipase from *Candida cylindracea* was dissolved in 9 g of water and subsequently added, with stirring, to the lecithin/oil mixture. This mixture was stirred at 47.5° C. for a period of 8.5 h and subsequently dried under a vacuum of 0.1 bar and at a temperature of 80° C.
Result:
The resultant product had an acetone-insoluble fraction of approximately 50% by weight and it contained 4% by weight of lysophosphatidylcholine, 5% by weight of monoacylglycerides and 6% by weight of diacylglycerides.

Example 7

225 g of crude lecithin were mixed with 275 g of soy oil and stirred at a temperature of 47.5° C. 0.25 g of lipase from *Candida cylindracea* was dissolved in 70 g of water and then added, with stirring, to the lecithin/oil mixture. This mixture was stirred at 47.5° C. and, after a reaction time of 8.5 h, dried under a vacuum of 0.1 bar and at a temperature of 60° C.
Result:
The resultant product had an acetone-insoluble fraction of approximately 30% by weight and it contained 2% by weight of lysophosphatidylcholine, 6% by weight of monoacylglycerides and 8.5% by weight of diacylglycerides.

Example 8

70 g of crude lecithin were mixed with 30 g of soy oil and stirred at a temperature of 60° C. 0.1 g of lipase from *Aspergillus niger* was dissolved in 12 g of water and then added, with stirring, to the lecithin/oil mixture. This mixture was stirred at 60° C. and, after a reaction time of 15 h, dried under a vacuum of 0.1 bar and at a temperature of 60° C.
Result:
The resultant product had an acetone-insoluble fraction of approximately 45% by weight and it contained 3% by weight of lysophosphatidylcholine, 5% by weight of monoacylglycerides and 10% by weight of diacylglycerides.

Example 9

70 g of crude lecithin were mixed with 30 g of hardened palm fat and stirred at a temperature of 45° C. 0.05 g of lipase from *Candida cylindracea* was dissolved in 10 g of water and subsequently added, with stirring, to the lecithin/oil mixture. This mixture was stirred at 45° C. and, after a reaction time of 8 h, dried under a vacuum of 0.1 bar and at a temperature of 60° C. The product was subsequently cooled and crystallized.
Result:
The emulsifier contained an acetone-insoluble fraction of approximately 45% by weight and, in addition, 3% by weight of lysophosphatidylcholine, 5% by weight of monoacylglycerides and 10% by weight of diacylglycerides.

Example 10 (Use Example)

The emulsifier produced according to example 9 was used in a standard method for producing margarine according to the formula below:

| | |
|---|---|
| 47.5% by weight | soy oil |
| 31.5% by weight | palm oil |
| 19.8% by weight | water |
| 0.1% by weight | cooking salt |
| 0.07% by weight | whey protein |
| 0.03% by weight | citric acid |
| 1.0% by weight | emulsifier |

Result:
A margarine was obtained which, with respect to texture, melting behavior and spreadability, is equivalent to standard margarines.

The invention claimed is:
1. A method for the enzymatic production of an emulsifier containing a lyso-phospholipid, mono- and diacylglycerides, consisting of
   a) charging a mixture of a phospholipid and a triacylglyceride,
   b) adding to the mixture of step a) an amount of an aqueous solution containing a lipase, a phospholipase or mixtures thereof such that the water content of the resulting mixture is between 3 and 15% by weight,
   subsequently,
   c) reacting the mixture obtained from method step b) at a temperature between 20° C. and 80° C. for a period of at least 2 hours, and after the reaction,
   d) drying the mixture of step c) to obtain an emulsifier.
2. The method according to claim 1, wherein said phospholipid is a lecithin.
3. The method according to claim 2, wherein said lecithin is a crude lecithin or a soy lecithin.
4. The method according to claim 1, wherein said triacylglyceride is a vegetable and/or animal oil.
5. The method according to claim 1, wherein in step a), a mixture having a phospholipid fraction between 10 and 80% by weight is charged.
6. The method according to claim 1, wherein in step a) a mixture having a triacylglyceride fraction between 20 and 90% by weight is charged.
7. The method according to claim 1, wherein the mixture in method step a) is brought to a temperature between 35° C. and 60° C.
8. The method according to claim 1, wherein in method step b), the lipase and/or phospholipase is of microbial origin.
9. The method according to claim 8, wherein said lipase and/or phospholipase is from *Candida* or *Aspergillus*.
10. The method according to claim 1, wherein the amount of a lipase, a phospholipase or mixtures thereof is 0.05 to 10 mg/ml.
11. The method according to claim 1, wherein step c), is carried out at a temperature between 40° C. and 50° C.
12. The method according to claim 1, wherein the reaction period in step c) is between 5 and 20 hours.
13. The method according to claim 12, wherein the reaction period in method step c) is between 8 and 12 hours.
14. The method according to claim 1, wherein the drying step d) is carried out at temperatures between 60° C. and 80° C.
15. The method according to claim 14, wherein the drying step d) is carried out in a vacuum.
16. The method according to claim 1, wherein a mixture of a lyso-phospholipid that is lysolecithin, mono- and diacylglycerides in fractions between 3.0 and 75% by weight of lysolecithin, 2.0 to 20% by weight of monoacylglycerides and 6.0 to 40% by weight of diacylglycerides is obtained.

17. The method according to claim 1, wherein a mixture having a ratio of phospholipid component:mono- and diacylglyceride component of 1:0.25 to 1:4.0 is obtained.

\* \* \* \* \*